US005308576A

United States Patent [19]

Green et al.

[11] Patent Number: 5,308,576

[45] Date of Patent: May 3, 1994

[54] INJECTION MOLDED ANVILS

[75] Inventors: David T. Green, Westport; Henry Bolanos, East Norwalk, both of Conn.

[73] Assignee: United States Surgical Corporation, Norwalk, Conn.

[21] Appl. No.: 779,071

[22] Filed: Oct. 18, 1991

[51] Int. Cl.$^5$ .............................. B22F 3/10

[52] U.S. Cl. .............................. 419/38; 227/76; 419/36; 419/41

[58] Field of Search .............................. 29/182; 75/235, 243, 75/246, 251, 252; 227/19, 76, 176, 178, 180; 264/63; 419/2, 3, 8, 23, 38, 36, 41

[56] References Cited

U.S. PATENT DOCUMENTS

| | | | |
|---|---|---|---|
| 3,490,675 | 1/1970 | Green | 227/76 |
| 3,499,591 | 3/1970 | Green | 227/76 |
| 4,708,741 | 11/1987 | Amaya | 75/251 |
| 4,765,950 | 8/1988 | Johnson | 419/2 |
| 4,964,907 | 10/1990 | Kiyota et al. | 75/235 |
| 5,014,899 | 5/1991 | Presty et al. | 227/180 |
| 5,015,289 | 5/1991 | Toda et al. | 75/229 |
| 5,028,367 | 7/1991 | Wei et al. | 264/63 |
| 5,032,354 | 7/1991 | Nakanishi | 419/23 |
| 5,040,715 | 8/1991 | Green et al. | 227/176 |

FOREIGN PATENT DOCUMENTS 0356131 2/1990 European Pat. Off. .

OTHER PUBLICATIONS

OAFT MIM Process Overview: Advanced Forming Technology Inc. pp. 1-6.

Metal Injection Molding at Advanced Forming Technology, John R. Baspervich & Richard C. Drewes: vol. 27, No. 2 (pp. 169-174), 1991.

Metal Injection Molded Parts Overview: Flo Met Inc., A subsidiary of Metal Powder Products, Inc. (1988).

Advanced Forming Metal Injection Molding (What it is; Why it is better) Advanced Forming Technology, Inc. (1988).

Advanced Forming Metal Injection Molding Design Guide Advanced Forming Technology, Inc. (1988).

New Process Technology for Cost-Effective Production of Metal Parts: Input Alloy; Dupont.

Designing for Metal Injection Molding: E. I. Du Pont de Nemours & Company, Inc. Remington.

EPO Communication dated Feb. 10, 1993, with attached Search Report from Corresponding Patent Application 92117703.6.

Patent Abstracts of Japan vol. 014, No. 172 (M0958) 4 Apr. 1990 & JP-A-2025501 (Kawasaki Steel Corp.) 29 Jan. 1990 abstract.

*Primary Examiner*—Donald P. Walsh
*Assistant Examiner*—John N. Greaves

[57] ABSTRACT

A method for making metal injection molded medical devices is disclosed. The method comprises melt blending, inject ion molding, and sintering a granulated hardenable metal feedstock.

11 Claims, 3 Drawing Sheets

10
12
15
11
14
13

INJECTION MOLDED ANVILS

FIELD OF THE INVENTION

The present invention relates to metal injection molded medical devices, and more particularly to a method of metal injection molding the working elements of surgical instrumentation.

BACKGROUND OF THE INVENTION

Jaws used for applying clips, grasping, dissecting and otherwise manipulating tissue are known. They are generally formed in the multistep process of machining metal blanks.

Similarly, surgical stapling instruments are well known in the art. For example, U.S. Pat. Nos. 3,499,591; 3,490,675; and 3,079,606, all of which are incorporated by reference, describe surgical stapling instruments for applying multiple rows of metal staples sequentially to body tissue.

Typically, such instruments employ a metal anvil member to form or crimp the staples. The anvil member possesses an upper surface with staple crimping depressions, or "pockets." When the staples are driven into the anvil the legs of the staple enter the pockets and are crimped, thereby securing the body tissue.

The anvil member is generally machined from a surgically acceptable strong metal alloy such as stainless steel. Then the staple pockets generally are coined into the finished anvil with a press. Finally the pockets are coated to make the pocket more suitable for interaction with the staple. This is an expensive multistep procedure which is not without fallouts in manufacturing anvils.

Alternatively, the pockets may be formed by electrical discharge machining. This process involves burning the pockets into the anvil with a copper electrode. This too is an extremely cost inefficient process. In order for the electrode to burn the pocket in the blank anvil, the electrode must be heated to a temperature that also causes the electrode itself to burn, requiring a new electrode for every anvil manufactured.

An anvil typically experiences pronounced forces when staples are advanced into contact with the staple forming surface thereof Anvils adapted for use with linear staplers of the type disclosed in U.S. Pat. No. 3,490,675, for example, may tend to bend, splay or otherwise move out of cooperative alignment with the staple cartridge in response to such forces. Steps have been taken to strengthen the anvils to resist such forces, e.g., by increasing wall thicknesses and the like, and/or to provide alignment means as described in U.S. Pat. No. 5,014,899.

However, the options available to manufacturers of surgical staplers which employ anvils become even more limited when the stapler is adapted for endoscopic use. In such cases, the anvil must be configured and dimensioned to pass through an endoscopic guide tube which typically has an inside diameter of 5 to 15 mm. Thus, the anvil typically exhibits a half-moon cross section and may be adapted to form one or more staple lines, e.g., from 15 to 60 mm in length. Such anvils must exhibit tremendous strength and be manufactured to close tolerances.

SUMMARY OF THE INVENTION

The present invention provides a more economical and accurate method to produce these medical devices.

In one of its aspects, the present invention provides a method of producing anvils for surgical equipment allowing for limited dimensional tolerances by employing a metal injection molding process which comprises melt blending a feedstock comprising metal powders having an average particle size up to about 10 microns with thermoplastic binder material to form pellets, which are then heated to a fluid state and injection molded in a mold configured and dimensioned to form a "green" molded part in the shape of an anvil. A majority of the binder is then removed and the part sintered.

In another embodiment, the present invention provides a method of producing jaws used for applying clips, grasping, dissecting, cutting and otherwise manipulating tissue allowing for limited dimensional tolerances by employing the above metal injection molding process.

DETAILED DESCRIPTION OF THE DRAWINGS

Figure 1:
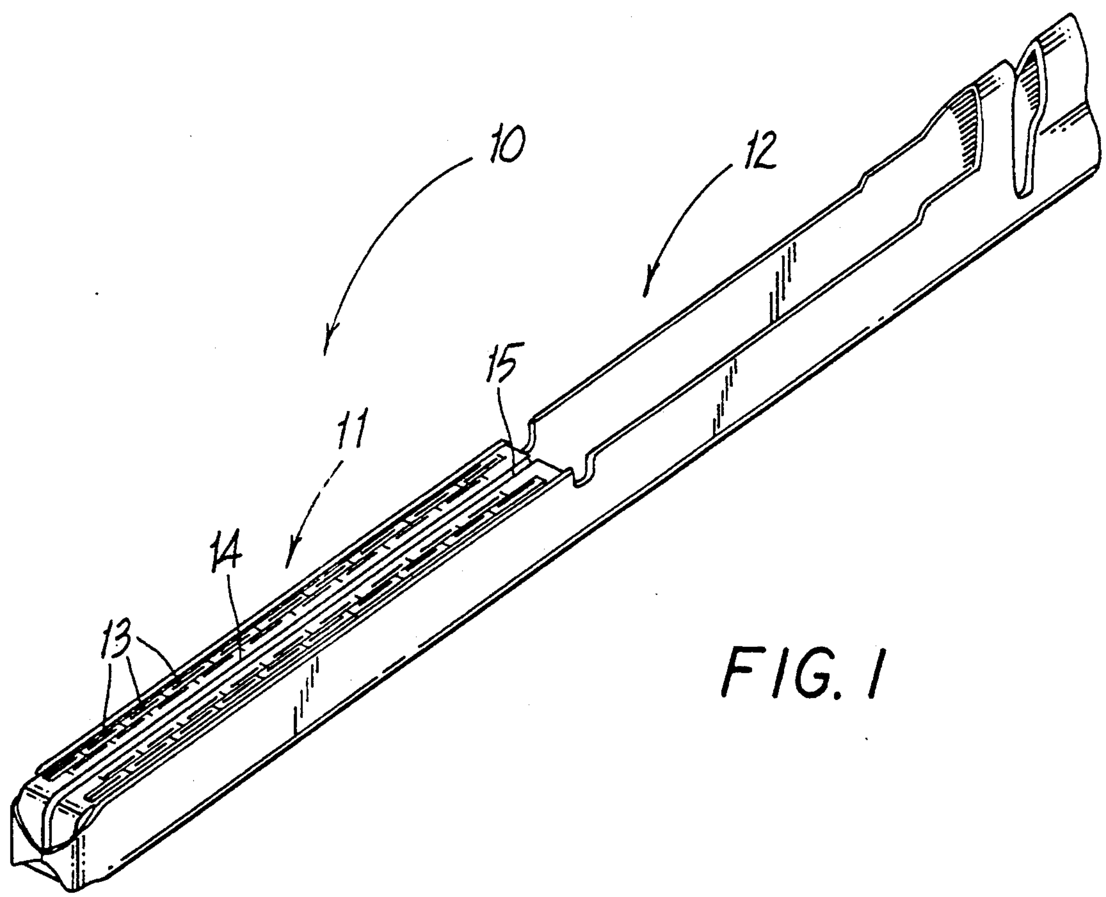
FIG. 1 is a perspective view of an anvil member.
Figure 2:
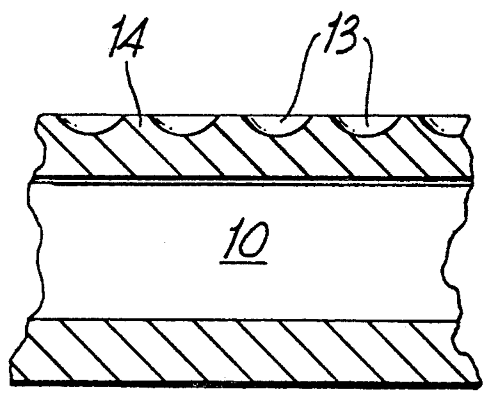
FIG. 2 is a sectional view of the anvil showing the staple crimping depressions or pockets.

FIGS. 1 and 2 illustrate an anvil member of the type commonly used in surgical stapling instruments. Anvil 10 is an elongated member having a distal position 11 with an upper staple forming surface 14 and a proximal portion 12. The staple forming upper surface 14 includes a plurality of staple crimping depressions or pockets 13. A knife slot 15 extends lengthwise along the upper surface 14 to permit longitudinal movement of a tissue cutting knife blade (not shown).

Figure 3:
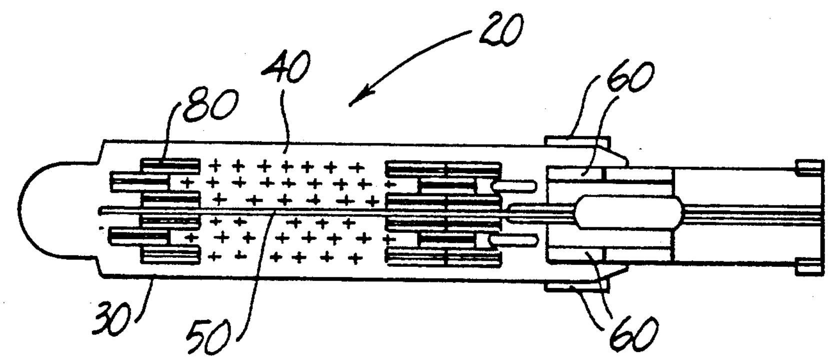
FIGS. 3-5 illustrate top, bottom and side views of an alternative anvil, respectively.
Figure 4:
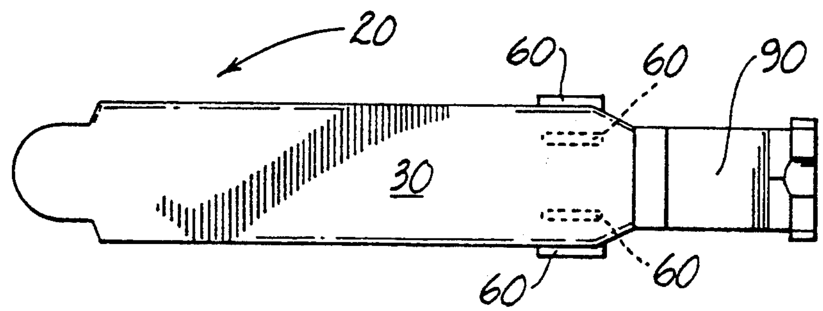
Figure 5:
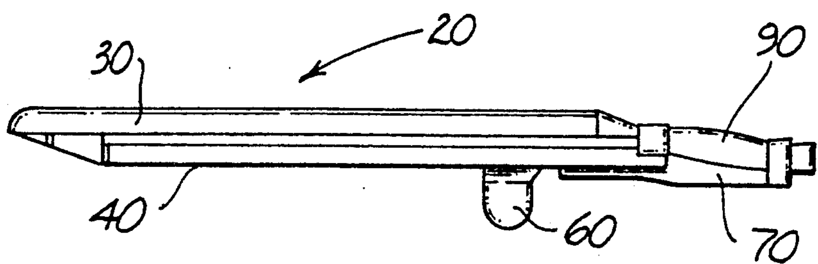

FIGS. 3-5 illustrate an anvil member of the type commonly used in endoscopic surgical instrumentation of the type disclosed in commonly assigned U.S. Pat. No. 5,040,715. Anvil 20 is an elongated piece which is pivotally mounted in relation to a support by means of a leaf spring (not shown). At its distal end, anvil 20 has an anvil plate 30 with a tissue contacting surface 40 having staple forming depressions 80 (See FIG. 4). At its proximal end, anvil 20 is provided with an upper camming surface 90 which is engageable with a corresponding top arcuate camming surface (not shown). Anvil plate 40 also has a longitudinal center groove 50 to permit passage of a knife (not shown). Anvil 20 provides one of the jaws of the instrument for clamping and securing the body tissue to be fastened. Preferably, anvil 20 is provided with one or more tissue stops 60 to help prevent over-insertion of tissue into the jaws. In a particularly advantageous embodiment shown in FIGS. 3-5 the anvil is provided with four tissue stops, two of which are disposed on the outer vertical surface of anvil plate 30 with the remaining two internally transversely positioned. This unique configuration allows for more accurate longitudinal alignment of the jaws and prevents twisting of the anvil upon closure. Anvil 20 is further provided with parallel aligning surfaces 70. These aligning surfaces are dimensioned to fit within projections on a cartridge housing (not shown) upon closure of the anvil 20. The engagement of the aligning surfaces 70 and the corresponding projections of cartridge housing serves to more accurately and securely align anvil 20 and the cartridge housing upon closure.

Further, as shown in FIG. 5, the horizontal plane formed by tissue contacting surface 40 intersects the horizontal plane formed by the camming portion of the proximal end of anvil 20 at an obtuse angle "α". This angular orientation precambers the anvil 20 and balances the closure force applied by the anvil 20 to the captured tissue.

A wide variety of staples and fasteners are contemplated for use with the present apparatus. When used with titanium fasteners, it has been found that forming of the fasteners in the staple forming depressions 80 is facilitated by applying a hard, relatively smooth surface on the anvil. This surface may be applied by electroless plating, with the surface being formed of a metallic alloy such as, for example, nickel, gold, silver, titanium nitride or chromium. Where nickel is used, the applied surface is preferably in the range of 100 u–2000 u in thickness with an optimum thickness of between 200 u–500 u. Ranges for other alloys may vary depending upon their inherent characteristics.

Figure 6:
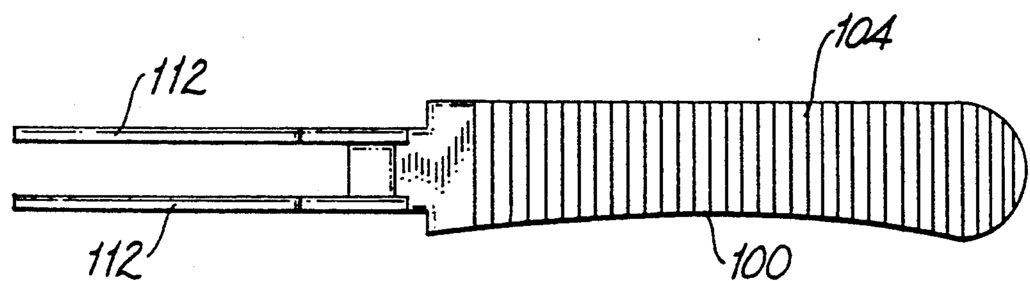
FIG. 6 is a plan view of an upper member of a grasper mechanism.
Figure 7:
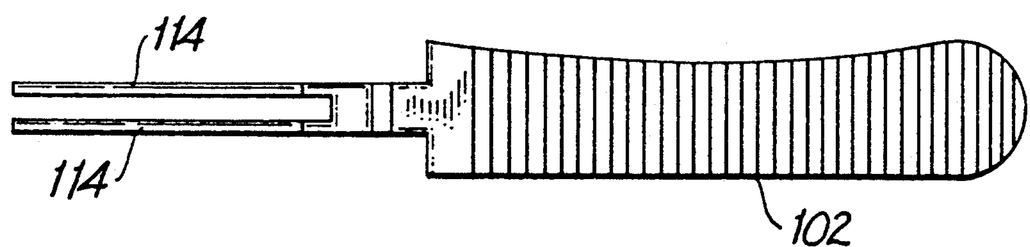
FIG. 7 is a plan view of a bottom member of a grasper mechanism.

FIGS. 6 and 7 illustrate a grasping mechanism of the type commonly used as a tool mechanism on endoscopic surgical instrumentation. FIGS. 6 and 7 illustrate a cooperating pair of grasping members 100 and 102 which are provided with serrations 104 to facilitate the grasping and holding of tissue. Projections 112 and 114 cooperate such that projections 112 are spaced greater than the distance between the projections 114 so that projections 114 may pass between projections 112 during opening and closing of the grasping device.

Suitable metals for use in the present invention include hardenable steels, such as heat treatable carbon containing steels.

Suitable binder materials are thermoplastics, including polyethylene, polypropylene, styrene, butadiene, polyamide, acrylate copolymers and waxes e.g. animal wax, china wax, wool wax, and synthetic waxes such as paraffin wax derivatives, etc., and mixtures thereof. Preferably the binder is about 60% polyethylene and about 40% wax.

The melt blending operations may be performed in conventional melt blending apparatus of both the batch and continuous type. They are often preferably conducted continuously in an extruder, by reason of the excellent properties of extruded material and the availability of extruders in commercial polymer processing facilities.

The injection molding machines which may be employed generally are those found in commercial polymer processing plants.

The binder may be removed from the "green" molded anvil by either exposure to solvent, heat or other extraction or separation means. Suitable solvents are commercially available and commonly known to remove the above mentioned binder material without interacting with the metal i.e., chloroform, methylene chloride, acetone, xylene, DMF and DMSO. Polymeric binder materials having large average molecular weights are generally thermally removed. Thermal removal of the binder material generally occurs in a vacuum oven. The oven is often modified to include means for measuring hydrocarbon levels. The "green" part is placed in the oven and heated until thermoplastic binder material is removed from the anvil as measured by the hydrocarbon level. The parts are then sintered, preferably without being moved, by then simply raising the temperature in the same oven to about 1000°–2500° C. Thermal removal of the thermoplastic binders and the sintering operation ranges from about 12 to about 48 hours.

The removal of the binder creates voids in the material which can facilitate subsequent treatment, such as coining to make staple pockets in the anvil. Nonetheless, the finish of the anvil remains smooth. Tbe anvil prepared by the method of the present invention may be molded with a blank surface or the mold may be configured and dimensioned such that staple pockets are formed in the anvil directly by the above described metal injection molding process. Suitable formations for the staple pockets include rectangular and star shaped pockets.

In order that those skilled in the art may be better able to practice the present invention, the following examples are given as an illustration of the preparation of the metal injection molded parts of the present invention. It should be noted that the invention is not limited to the specific details embodied in the examples and further that all parts are by weight.

Example 1

A feedstock was made by extruding granulated Fe-2% Ni Steel having an average particle size of up to about 10 microns commercially available thermoplastic binder of about 60% polyethylene and about 40% wax. This feedstock was then heated until viscous enough to be injected into a mold configured and dimensioned to form a "green" part in the shape of an anvil 20 described above, absent the staple crimping pockets. This "green" part had its major axis three inches in length. The "green" part was then placed in a vacuum oven. The oven was heated to remove the thermoplastic binders. The part was then sintered in the same oven.

Example 2

The procedure of Example 1 was repeated except the mold was configured and dimensioned to create an anvil member having rectangular staple crimping pockets.

Example 3

The procedure of Example 1 was repeated except the mold was configured and dimensioned so as to create an anvil member having a major axis of 7 inches in length.

Example 4

The procedure of Example 3 could be repeated except the mold could be configured and dimensioned to create an anvil member having star shaped staple crimping pockets.

Example 5

The procedure of Example 1 may be repeated except that the mold could be configured and dimensioned to create a "green" part in the shape of a grasping member described above.

What is claimed is:

1. A method for producing a metal injection molded medical device in the shape of a grasping member comprising:

a. melt blending a feedstock, comprising a hardenable metal with a thermoplastic binder material;
b. injection molding the feedstock in a mold configured and dimensioned to form a medical device;
c. removing a majority of the binder material; and
d. sintering the medical device.

2. A method according to claim 1, wherein the melt blending process is extrusion.

3. A method according to claim 1, wherein the binder is removed by a solvent.

4. A method according to claim 3, wherein the solvent is selected from the group consisting of chloroform, methylene chloride, acetone, xylene, DMF and DMSO.

5. A method according to claim 1, wherein the binder is removed by thermal means.

6. A method according to claim 5, wherein the thermal means comprises a vacuum oven heated from about 1000 to about 2500° C.

7. A method according to claim 1, wherein the metal has an average particle size of up to about 10 microns.

8. A method for producing a metal injection molded medical device comprising:
a. melt blending a feedstock, comprising a hardenable metal with a thermoplastic binder material;
b. injection molding the feedstock in a mold configured and dimensioned to form a medical device;
c. removing a majority of the binder material; and
d. sintering the medical device is in the shape of a member selected from the group consisting of an anvil, an anvil having a blank surface, an anvil having pockets configured in the shape of a rectangle, and an anvil having pockets configured in the shape of a star.

9. A method according to claim 8, wherein the device has a major axis of about 7 inches.

10. A medical device produced by the method of claim 1 wherein the device is a grasping member.

11. A method according to claim 8, wherein said thermoplastic binder material further comprises a material selected from the group consisting of animal wax, china wax, wool wax, paraffin wax, and mixtures thereof.

* * * * *